United States Patent [19]

Scancarella et al.

[11] Patent Number: 5,776,441
[45] Date of Patent: Jul. 7, 1998

[54] LIP TREATMENT CONTAINING LIVE YEAST CELL DERIVATIVE

[75] Inventors: Neil Scancarella, Wyckoff; Harold Pahlck, Waldwick; Maha Raouf, Franklin Lakes, all of N.J.

[73] Assignee: Avon Products, Inc., New York, N.Y.

[21] Appl. No.: 705,779

[22] Filed: Aug. 30, 1996

[51] Int. Cl.⁶ ............... A61K 7/00; A61K 7/04
[52] U.S. Cl. ............... 424/61; 424/401
[58] Field of Search ............... 424/60, 61, 64, 424/401, 63, 520, 78.02; 514/714

[56] References Cited

U.S. PATENT DOCUMENTS

| 2,320,478 | 6/1943 | Sperti | 167/91 |
| 2,320,479 | 6/1943 | Sperti | 167/58 |
| 4,873,078 | 10/1989 | Edmundson et al. | 424/64 |
| 5,023,090 | 6/1991 | Levin | 424/520 |
| 5,204,105 | 4/1993 | Mausner | 424/401 |
| 5,223,491 | 6/1993 | Donzis | 514/54 |
| 5,643,587 | 7/1997 | Duffy et al. | 424/401 |

OTHER PUBLICATIONS

"The Manufacture of Efficacious Cosmetic Ingredients Utilizing Biochemical Processes of Yeast" by Geoffrey J. Brooks.

"Skin Health and Respiration" by Elton S. Cook, Jan. 1939.

"BIODYNES® TRF Live Yeast Cell Derivative" brochure dated Fall 1994.

"BIODYNES® TRF Powder" specification dated Jan. 31, 1995.

"Skin Protectant Drug Products for Over-the Counter Human Use; Tentative Final Monograph" (48 FR 6820) dated Feb. 15, 1983.

*Primary Examiner*—Thurman K. Page
*Assistant Examiner*—Sharon Howard
*Attorney, Agent, or Firm*—Ohlandt, Greeley, Ruggiero & Perle

[57] ABSTRACT

A lip treatment containing a bioyeast ingredient, such as a live yeast cell derivative, and a suitable carrier. The live yeast cell derivative is produced by lysing and concentrating the cell contents of yeast cells subjected to an extended period of non-lethal stress such as is induced by exposure to certain wavelengths of ultraviolet light. The lip treatment rapidly moisturizes, smoothes, and heals the lips, and provides for rapid exfoliation of chapped cells on the lips. Thus, the treated lips are restored to a soft and supple condition.

20 Claims, No Drawings

LIP TREATMENT CONTAINING LIVE YEAST CELL DERIVATIVE

The present invention relates generally to cosmetic formulations containing a bioyeast derivative, which formulations are suitable for application to the lips. More particularly, this invention relates to a lipstick or pomade having a live yeast cell derivative that acts as a moisturizing, healing and smoothing agent.

BACKGROUND OF THE INVENTION

The skin on the lips is structurally different from skin elsewhere on a human's body. Lips have a thinner stratum corneum and a lesser amount of lipids than non-lip skin or typical skin. This allows water to easily pass through and dissipate from the lips. In fact, water loss through the lips is 10 times greater than water loss through typical skin. This makes the lips more prone to dryness and, over time, to greater damage.

Lip stratum corneum also has a high turnover rate, meaning that the corneocytes are constantly shedding. As part of the shedding process, dead cells cluster in flakes on the surface of the lips. When the lips are dry, these flakes are more evident. In addition, lips have a lower number of melanocytes, or melanin producing cells, in comparison to typical skin. In the absence of large numbers of these melanocytes, lips have less melanin and are more prone to UV induced sun damage.

Accordingly, consumers demand an effective treatment for the lips that moisturizes, heals, and smoothes the vulnerable and delicate surface of the lips. Most lip products on the market consist of occlusive oils or waxes that limit the amount of moisture that escapes from the lips. These products do not address any underlying dryness, and merely prevent further desiccation. Some products also contain moisturizing ingredients and healing ingredients. The efficacy of such products varies widely.

Yeast cell derivatives are known in the art for general skin treatment. U.S. Pat. No. 2,320,478 to Sperti discloses the live yeast cell derivative that is a preferred component of the present invention, and discloses its general topical application in lotions, creams and oils. The patent teaches that the live yeast cell derivative enhances skin respiration [col. 2, lines 10–18]. However, normal enhanced lip tissue respiration would presumably lead to increased moisture loss, and therefore, this derivative would not appear to be beneficial to lip tissue. Because the lips are so vulnerable to moisture loss, any likely increase in the rate of moisture loss would be very detrimental in a cosmetic product and would tend to outweigh any other benefits provided by the product.

It has been found, surprisingly, that this live yeast cell derivative, when incorporated into lip preparations, such as lip treatments, lip balms, lipsticks or pomades, has a dramatic moisturizing, healing and smoothing effect on lips, especially on dry lips. The live yeast cell derivative is produced by lysing and concentrating the cell contents of yeast cells subjected to an extended period of non-lethal stress such as is induced by exposure to certain wavelengths of ultraviolet light.

The assignee of the present application has a pending U.S. patent application Ser. No. 8/602,004, filed Feb. 15, 1996. The pending application is directed to a composition containing a live yeast cell derivative in combination with other active ingredients such as magnesium ascorbyl phosphate, tocopherol acetate and retinol palmitate in a carrier for the treatment of skin discolorations under the eyes.

SUMMARY OF THE INVENTION

Against the foregoing background, it is a primary object of the present invention to provide a lip preparation containing an effective amount of a live yeast cell derivative.

It is another object of the present invention to provide such a lip preparation that has moisturizing, healing and smoothing properties.

It is yet another object of the present invention to provide such a lip preparation that results in rapid exfoliation of chapped lip cells and restores a soft, supple texture to the lips.

It is a further object of the present invention to provide a live yeast cell derivative that is compatible with cosmetic lip carriers so that it is suitable for use in lip treatments, such as lipsticks, lip balms and pomades.

To the accomplishment of the foregoing objects and advantages, the present invention, in brief summary, comprises a live yeast cell derivative in a cosmetic carrier suitable for application to the lips.

The invention further comprises a composition containing a live yeast cell derivative derived from yeast cells that have been subjected over time to a non-lethal trauma. This induces the yeast cells to produce unique healing compounds that are contained in the resulting yeast cell derivative. The composition further comprises a suitable carrier for application to the lips.

DESCRIPTION OF THE PREFERRED EMBODIMENTS

The yeast cell derivative of the present invention is substantially described in the U.S. Pat. No. 2,320,478 to Sperti, discussed above. That patent is hereby incorporated by reference. The present invention includes topical compositions that contain a live yeast cell derivative (hereinafter also "LYCD") as an ingredient in a suitable carrier for application to the lips.

LYCD is a highly soluble material. This LYCD is produced, preferably, according to the following method. Yeast cultures are placed in a fermenter. They are brought to viability by the use of the appropriate nutritious media with thorough aeration under controlled temperature conditions. The living yeast cells are then subjected to an "injury" process such as irradiating them with UV light of a specified wavelength (286 nm). The cells respond to the debilitating effects of the UV light by producing various protective substances.

The "injury" process is continued until the complex biochemical protective mechanisms are complete (this can take several days). The fermentation is stopped by breaking down the yeast cell walls utilizing a proteolytic enzyme. The bulk of the insoluble cell wall material is removed by centrifugation, leaving cellular protoplasm behind. The protoplasmic derivative is then concentrated and assayed for biological activity. The LYCD derivative can be concentrated by freeze drying or spray drying. It is provided commercially as a fine hygroscopic powder or as a filtered solution. The preferred form is a refined powder.

The LYCD powder or solution can then be incorporated into various carriers suitable for application to the lips. LYCD is preferably present at about 0.01 to 15.00% by weight of the total weight of the lipstick or other composition. At concentrations greater than 15%, the cost of the LYCD becomes prohibitive. In a preferred embodiment, the base is about 70.00% to about 90.00% by weight of the total weight of the composition, the LYCD is about 0.01% to about 15.00% by weight, colorants are up to about 15.00% by weight, fragrances up to about 3.00% by weight, and other ingredients, such as skin protectants, are about 0.01% to about 10.0% by weight. The skin protectants should include allantoin in an amount about 0.50% to about 2.0% by weight.

A further preferred lip composition according to the present invention includes a live yeast cell derivative and a suitable carrier or base, wherein the live yeast cell derivative is a saccharomyces lysate derivative. Preferably, this preferred embodiment lip product comprises from about 0.01% to about 15% live yeast cell derivative. The carrier or base preferably comprises about 60% to about 90% and, most preferably, 76% by weight of the total weight of the lip composition, and moisturizers, which may make up part or most of the carrier, comprise about the same amount.

Preferred moisturizers include lanolin, vegetable oil, castor oil, isopropyl palmitate, mineral oil, petrolatum, avocado oil, soybean oil, caprylic/capric triglycerides, diisopropyl dimerate, methicone or a combination thereof.

A preferred lip composition of the present invention also includes about 0.60% of a healing agent. Preferred healing agents include vitamin E, allantoin, candelilla wax, aloe vera, petrolatum, calamine, dimethicone, cocoa butter, shark liver oil, glycerin, zinc oxide, aluminum hydroxide, kaolin, zinc acetate, zinc carbonate or a combination thereof.

A preferred lip composition may also include about 15.0% percent of an occlusive wax. Preferred waxes include candelilla wax, ceresine wax, ozokerite, lanolin wax, beeswax, paraffin, microcrystalline wax, animal wax, plant wax, synthetic wax, mineral wax, Japan wax, spermaceti, sunflower wax, orange wax, shellac wax, rice wax, jojoba wax, rose wax, jasmine wax or a combination thereof.

Additionally, certain preferred lip compositions may include a colorant or additional active ingredients. Preferred active ingredients include allantoin, aloe vera, elastin, collagen, vitamin E and derivatives thereof, vitamin A and derivatives thereof, liposomes, sodium hyaluronate, water, botanical extracts, phospholipids, silk powder, evening primrose oil, cholesteryl blo glutamate, hyaluronic acid, rose hips oil, lauroyl lysine or a combination thereof.

A most preferred lip composition according to the present invention includes about 70% to about 90% by weight of a base including hydroxylated lanolin and polybutene, and about 0.01% to about 15% by weight of a live yeast cell derivative. Optimally the LYCD is present at about 0.5% by weight. Most preferably, this composition also includes about 2.0% to about 9.0% by weight of colorants, about 76% by weight of base.

The following is an illustrative preferred embodiment, with all percentages expressed as relative weight of the ingredient to total weight of the composition (this applies to Examples 2–7 as well).

EXAMPLE 1

Treatment Lipstick

|  | Wt. % |
| --- | --- |
| LYCD | 0.50 |
| Base | Approx. 76.45 |
| May include the following: |  |
| Ozokerite 170-D | 5.50 |
| Polyethylene-Linear PL | 3.00 |
| Micro Wax White | 5.00 |
| Lanolin-Low Odor | 12.00 |
| Diglyceryl Diisostearate | 11.50 |
| Sucrose Acetate Isobutyrate | 10.00 |
| Isopropyl Isostearate | 5.00 |

-continued

|  | Wt. % |
| --- | --- |
| Silica Bead S-700 - Japan | 2.00 |
| Propyl Paraben | 0.20 |
| Diisopropyl Dimerate | 22.25 |
| Total Colorants | Approx. 13.00 |
| May include the following: |  |
| Pigment | 4.00 to 12.00 |
| Barium Sulfate | 0.00 to 3.50 |
| Pearl | 0.00 to 7.00 |
| Mica Fine | 1.00 to 4.00 |
| Other Ingredients | Approx. 9.925 |
| May include the following: |  |
| Allantoin | 0.60 |
| Other skin protectants | 9.325 |
| Fragrance | Approx. 0.125 |

The above base ingredients are merely representative of what one of ordinary skill in the art would include as base ingredients in a treatment lipstick.

The lipstick of Example 1 was assessed, under blind conditions, to test the overall acceptability, aesthetics, and perceived performance of this embodiment of the present invention. A two-week consumer home-use test was conducted. Fifty-six participants were surveyed after seven and fourteen days of use. All participants were female, aged 25–55, and described themselves as having dry or chapped lips, but not as having cracked or bleeding lips. The following table summarizes the results of the survey. The results are expressed in percent of respondents asked. Where entries are left blank, respondents were not tested on that item on that date.

| Test Item | 7 days | 14 days |
| --- | --- | --- |
| Just the right amount of color deposited | 74% |  |
| Very/moderately even color | 95 |  |
| Not too/Not at all greasy | 91 |  |
| Acceptable | 100 |  |
| Very/Moderately attractive appearance on application | 73 |  |
| Very/Moderately visible product | 90 |  |
| Neither liked nor disliked taste | 73 |  |
| Very/Moderately gentle | 90 | 93 |
| Very/Moderately effective moisturizer | 80 | 75 |
| Lasts much/Lasts somewhat longer than expected | 66 | 62 |
| Very/Moderately acceptable wear | 76 | 79 |
| Repairs Your Lips - Agree | 78 | 77 |
| Gives Lips a Fuller Appearance - Agree | 62 | 64 |
| Retexturizes Lips to their More Natural Shape - Agree | 56 | 55 |
| Makes Lips Feel Supple - Agree | 79 | 84 |
| Makes Lips Look Younger - Agree | 53 | 58 |
| Minimizes the Appearance of Lip Lines/Wrinkles- Agree | 60 | 64 |
| Makes Lips Look Smoother - Agree | 75 | 80 |
| Is Ultra Creamy - Agree | 90 | 89 |
| Glides on Smoothly - Agree | 100 | 96 |
| Prevents Lips from Becoming Dry - Agree |  | 84 |
| Prevents Lips from Peeling - Agree | 74 | 76 |
| Provides Extraordinary Lush Color - Agree | 74 | 73 |
| Redefines Your Lips' Natural Shape - Agree | 64 | 64 |
| Makes Lips Appear Plumper - | 52 | 57 |

-continued

| Test Item | 7 days | 14 days |
| --- | --- | --- |
| Agree | | |
| Makes Lips Feel More Supple - Agree | 78 | 82 |
| Is Non-feathering - Agree | 55 | 71 |
| Provides Full Coverage - Agree | 93 | 91 |
| Is Long Wearing - Agree | 83 | 82 |
| Improves the Appearance of Lips - Agree | 79 | 82 |

These data support the conclusion that respondents noticed significant improvement in the appearance of their lips at both 7 and 14 days of use. With continuous use, the product of Example 1 effectively corrected peeling, chapped and dry lip conditions that troubled these respondents.

Additional testing was performed to determine the ability of the preferred embodiment of Example 1 to enhance moisture content and prevent moisture loss when applied to the lips.

Example 1, as discussed above, includes LYCD, occlusive waxes, and moisturizing ingredients such as cholesteryl blo glutamate and aloe vera gel.

| | One hour | Two hours |
| --- | --- | --- |
| Moisture content | +432% | +305% |
| Decrease in water loss | 31% | 28% |

The study was conducted on a panel of 15 women aged 25–45 years old. They were instructed to refrain from wetting their lips for the duration of the study. After a 30 minute period of acclimation, a wooden tongue depressor was inserted across the mouth of each panelist as a physical barrier against unintentional wetting of the lips. After 5 minutes, baseline values were measured. Once the baseline measurements were collected, panelists applied the product of Example 1 in their normal fashion. Measurements were collected after one hour and after two hours from the lower lip of each panelist.

Moisture content of the lips was measured using the Skicon-200 Conductance meter that measures the conductance of skin which is a reflection of water content. Measurements were taken at baseline (after acclimation and before lipstick application). Participants had lip Skicon values of approximately 50. Measurements were also taken one hour and two hours after lipstick application. A series of 5 readings was made for each site during each measurement, and the average value computed. Higher values indicate increased hydration levels and moisturization. Average measurements obtained were as follows:

Baseline: 58.4
One hour: 310.5
Two hours: 236.5

As summarized above, this reflects an increase in moisturization of 432% after one hour and 305% after two hours.

Water loss or barrier function of the lips was measured using the Servomed Evaporimeter. Transepidermal water loss (TEWL) is a reflection of the barrier function of the lip stratum corneum. A defective barrier results in high water loss values. Products with occlusive agents decrease water loss and provide a barrier. Therefore, lowered TEWL values after lipstick application indicates prevention of water loss due to the occlusivity of the product.

A third study was undertaken to determine the clinical efficacy of the Example 1 product and its ability to repair dry, damaged lips. The test was conducted on fifteen women, aged 18–55 years old, with dry lips who usually use lip balm, in the dry and cold environment of Winnipeg, Canada. Participants were instructed not to use any lip treatment products for three days before the outset of the test and to use the product of Example 1 for two weeks, in the same manner in which they use their regular lipstick. Each participant was given one colored lipstick and one clear lipstick. Subjects applied their choice of colored or clear lipstick at least every two hours and after every meal. They also refrained from using any other lip products for the duration of the study. Subjects were instructed to apply only the clear lipstick on the days their lips were to be evaluated, two hours or more before the visual evaluation, to facilitate examination of the lips. Subjects were also instructed to avoid contact with water during that period. The lips were visually evaluated by an expert grader on days 0, 3, 7, 10, and 14 of the treatment.

High quality photography was used to grade and record the participants' lips over the course of the study. The photography showed an obvious decrease in dryness and scales during the treatment. Lips looked moisturized, smooth, full and plump after 7 and 14 days of treatment. In addition to an obvious decrease in scales, there appears to be an increase in the crisscross patterns of the tiny lines or a quilting pattern upon moisturization. The appearance of the quilting pattern indicates the normalization of the lip texture to a normal, healthy condition.

| Days | Percent of Subjects | Percent Improvement |
| --- | --- | --- |
| 3 | 93 | 33 |
| 7 | 100 | 37 |
| 10 | 100 | 34 |
| 14 | 93 | 54 |

Thus, three days after the beginning of the treatment, these formulations improved dryness in 93% of the subjects. Improvement continued for 14 days with the greatest amount of reduction in dryness observed on day 14 (54% from baseline).

The LYCD component can be incorporated in all acceptable lip product carriers, such as pot gloss, wand lip gloss, lip balm or pomade, lip conditioner and other lipsticks, with varying levels of colorants. The amount of the LYCD component in a Pot Gloss is preferably about 0.50% to about 15.0% by weight of the total weight of the composition. The amount of base can preferably range from about 40% to about 90%. The following are examples of various lip product compositions and carriers that can include the LYCD component.

EXAMPLE 2

Pot Gloss

| | Wt. % |
| --- | --- |
| LYCD | 1.00 |
| Base | |
| May include the following: | |
| Candelilla Wax | 2.0 |
| Ceresine Wax 1670 | 2.0 |
| Hydroxylated Lanolin | 12.0 to 27.0 |

-continued

| | Wt. % |
|---|---|
| Ozokerite | 3.0 |
| Benzoic Acid | 0.2 |
| PPG-5 Lanolin Wax | 8.0 |
| Soybean Oil-Maleated (UNF) | 2.0 |
| Propylene Glycol Ricinoleate | 2.7 |
| Polybutene | 25.0 |
| Caprylic/Capric Triglycerides | 13.3 |
| Ammonium Glycyrrhizinate | 0.35 |
| Castor Oil | Q.S. to 100.0 |
| Lecithin | 1.3 |

The composition may preferably include the following additional ingredients in the following preferred amounts: about 0.10% to 10.0% of colorants, and about 10% to 30% of other non-base ingredients, such as powder, vitamins and fragrances, flavors, oils, waxes, esters, preservatives and water.

The colorants may include pigments & barium sulfate (about 1.2% to about 5.0%) and pearls (up to about 7.0%). Other ingredients may include ethylhexyl-methoxycinnamate, benzophenone or other sunscreens (about 1.00% or higher). The vitamins may include vitamin E (about 0.05%), vitamin C, beta carotene and vitamin A palmitate 1.65×10 (about 0.01%). About 0.1% of fragrance or flavor may be included. As in each example, trace amounts of other ingredients may also be included.

EXAMPLES 3 and 4

Lip Pomade

In Lip Pomades, the LYCD is preferably about 0.30% to about 1.50% by weight of the total weight of the composition, and preferably 1.00% by weight. The base is preferably about 60.0% to 95.0% and may include the following:

| | Wt % | |
|---|---|---|
| | Ex. 3 | Ex. 4 |
| Castor Oil - preserved | 39.310 to 42.960 | 44.780 to 44.960 |
| Dewaxed Lanolin | 4.400 | 4.400 |
| Isopropyl Palmitate | 14.300 | 14.300 |
| Beeswax | 10.400 | 10.400 |
| Ozokerite 170-D | 2.700 | 2.700 |
| Fatty Acid Triglycerides | 9.600 | 9.600 |
| Candelilla Wax | 7.200 | 7.200 |
| Cetyl Alcohol | 3.300 | 3.300 |
| Butylated Hydroxyanisole or Butylated Hydroxytoluene | 0.010 | 0.010 |
| Ammonium Glycyrrhizinate | 0.350 to 1.000 | 0.150 to 0.350 |
| Benzoic Acid | 0.200 | 0.200 |
| Menthol-Odorless-Japan | — | 0.500 |

The composition may also include the following ingredients in the following preferred ranges: colorants, such as pigments (about 0.05% to about 15.0%); other ingredients such as ethylhexyl-methoxycinnamate (about 3.00%) or other sunscreens such as benzophenone; and fragrance/flavor (about 1.50% to about 3.00%).

EXAMPLE 5

Volatile Base Lipstick

In a Volatile Base Lipstick, the LYCD preferably makes up about 0.30% to about 5.00%, and the base preferably makes up about 60% to about 90% of this volatile base lipstick composition.

| | Wt. % |
|---|---|
| LYCD | 1.00 |
| Base | |
| May include the following: | |
| Polyethylene | 7.00 |
| Ozokerite | 4.25 to 6.25 |
| Diisostearyl Malate | 8.50 |
| Sucrose Acetate Isobutyrate | 13.00 |
| Microcrystalline Wax | 1.00 |
| Stearyl Alcohol | 0.001 |
| Ethylhexyl Palmitate | 2.00 |
| Allantoin | 0.20 |
| Vitamin E | 0.05 |
| Cyclomethicone-Tetramer | 35.00 |
| Nylon Powder-Spherical | 3.00 |
| Diisopropyl Dimerate | 6.9969 to 8.9969 |

LYCD can be in the range of about 0.50% to about 2.0% by weight. Colorants of approximately 16% may include, for example, D&C Red #21 (0.30%), pigments/pearls (16.70%), and extenders (0.00 to 0.0001%).

EXAMPLE 6

Lip Conditioner

In Lip Conditioners, the LYCD preferably makes up about 0.10% to about 2.00%, and the base preferably makes up about 70% to about 95% of this lip conditioner formulation.

| | Wt. % |
|---|---|
| LYCD | 1.00 |
| Base | |
| May include the following: | |
| Demineralized Water | 58.94 |
| Tetrasodium EDTA | 0.10 |
| Glycerin | 5.00 |
| Xanthan Gum | 0.10 |
| Grape Seek Oil | 5.00 |
| Sunflower Seed Oil | 5.00 |
| Vegetable Oil Triglyceride | 3.00 |
| Squalane | 2.00 |
| Soya Sterols | 1.00 |
| POE (40M) Stearate | 2.00 |
| Myristyl Myristate | 2.00 |
| Cetyl Alcohol | 2.00 |
| Glyceryl Monostearate | 2.50 |
| Iodopropynylbutyl Carbamate | 0.30 |
| Cyclomethicone | 3.00 |
| Ethylhexyl-methoxycinnamate | 4.50 |
| Liposome Vitamin A/C/E/Beta Carotene | 0.02 |
| Benzyl Alcohol | 1.00 |
| Benzophenone 3 | 1.00 |
| Aloe Vera Gel Powder | 0.01 |
| Wild Chamomile | 0.03 |
| 2-phenoxyethanol | 0.50 |

EXAMPLE 7

Intensive Lip Balm

In Intensive Lip Balms, the base preferably makes up about 75% to about 95%, and the LYCD preferably makes up about 0.10% to about 10.00% of the following intensive lip balm formulation. Fragrance is preferably up to about 5.00% of this formulation.

|  | Wt. % |
|---|---|
| LYCD | 0.50 |
| Base | |
| Petrolatum Low Taste | 84.95 |
| Benzyl Alcohol | 0.50 |
| Ethylhexyl-methoxycinnamate | 7.50 |
| Benzophenone 3 | 3.00 |
| Paraffin Wax | 1.00 |
| Butylated Hydroxytoluene or Butylated Hydroxyanisole | 0.50 |
| Vegetable oil triglycerides | 2.00 |
| Fragrance | 0.50 |

The invention having been thus described with particular reference to the preferred forms thereof, it will be obvious that various changes and modifications may be made therein without departing from the spirit and scope of the invention as defined in the appended claims.

What we claim is:

1. A lip composition comprising:
    yeast cell protoplasm from yeast cells that have been subjected to an injury process, said yeast cell protoplasm being substantially free of yeast cell wall material; and
    a suitable carrier.

2. The lip composition of claim 1, wherein said yeast cell protoplasm is a saccharomyces lysate derivative.

3. A lip product comprising from about 0.01% to about 15% yeast cell protoplasm.

4. A lip composition comprising yeast cell protoplasm and a suitable carrier, whereby after application to a human's lips provides healing, smoothing and moisturizing properties to the lips.

5. A lip composition comprising about 76% by weight of the total weight of the lip composition of a carrier and about 0.01% to about 15% of a protoplasmic yeast cell concentrate.

6. The lip composition of claim 5, further comprising about 75% of a moisturizer.

7. The lip composition of claim 6, wherein said moisturizer is selected from the group consisting of lanolin, vegetable oil, castor oil, isopropyl palmitate, mineral oil, petrolatum, avocado oil, soybean oil, caprylic/capric triglycerides, diisopropyl dimerate, methicone and a combination thereof.

8. The lip composition of claim 5, further comprising about 0.60% of a healing agent.

9. The lip composition of claim 8, wherein said healing agent is selected from the group consisting of vitamin E, allantoin, candelilla wax, aloe vera, petrolatum, calamine, dimethicone, cocoa butter, shark liver oil, glycerin, zinc oxide, aluminum hydroxide, kaolin, zinc acetate, zinc carbonate and a combination thereof.

10. The lip composition of claim 5, further comprising about 15.0% of an occlusive wax.

11. The lip composition of claim 10, wherein said occlusive wax is selected from the group consisting of candelilla wax, ceresine wax, ozokerite, lanolin wax, beeswax, paraffin, microcrystalline wax, animal wax, plant wax, synthetic wax, mineral wax, Japan wax, spermaceti, sunflower wax, orange wax, shellac wax, rice wax, jojoba wax, rose wax, jasmine wax and a combination thereof.

12. The lip composition of claim 5, further comprising a colorant.

13. The lip composition of claim 5, further comprising an additional active ingredient selected from the group consisting of allantoin, aloe vera, elastin, collagen, vitamin E and derivatives thereof, vitamin A and derivatives thereof, vitamin C and derivatives thereof, liposomes, sodium hyaluronate, water, botanical extracts, phospholipids, silk powder, evening primrose oil, cholesteryl blo glutamate, hyaluronic acid, rose hips oil, lauroyl lysine and a combination thereof.

14. The lip composition of claim 5, wherein one hour after application of said composition to lips there is about a fourfold increase in moisturization of the lips.

15. The lip composition of claim 5, wherein said composition, once applied to lips, provides for rapid exfoliation of chapped cells on the lips.

16. A lip composition comprising:
    about 70% to about 90% by weight of the total weight of the lip composition of a base including hydroxylated lanolin and polybutene; and
    about 0.01% to about 15.0% by weight of yeast cell protoplasm from yeast cells that have been subjected to an injury process, said yeast cell protoplasm being substantially free of yeast cell wall material.

17. The lip composition of claim 16, further comprising about 2.0% to about 9.0% by weight of colorants.

18. The lip composition of claim 16, wherein the base is about 76% by weight.

19. The lip composition of claim 16, wherein said yeast cell protoplasm is about 0.5% by weight.

20. A method of treating lips including applying to the lips a composition comprising a substantially cell wall-free yeast cell protoplasm and a suitable carrier.

* * * * *